(12) United States Patent
Huang

(10) Patent No.: US 8,034,242 B2
(45) Date of Patent: Oct. 11, 2011

(54) DIALYSIS DEVICE

(75) Inventor: Tai-Nang Huang, Lexington, MA (US)

(73) Assignee: Linden Technologies, Inc., Woburn, MA (US)

( * ) Notice: Subject to any disclaimer, the term of this patent is extended or adjusted under 35 U.S.C. 154(b) by 0 days.

(21) Appl. No.: 12/581,682

(22) Filed: Oct. 19, 2009

(65) Prior Publication Data

US 2010/0264085 A1 Oct. 21, 2010

Related U.S. Application Data

(62) Division of application No. 11/281,236, filed on Nov. 17, 2005, now Pat. No. 7,604,739.

(60) Provisional application No. 60/629,000, filed on Nov. 18, 2004.

(51) Int. Cl.
*B01D 63/06* (2006.01)
*B01D 61/28* (2006.01)

(52) U.S. Cl. ........... 210/321.78; 210/321.6; 210/321.87; 210/323.2

(58) Field of Classification Search ............... 210/321.6, 210/321.78, 321.87, 645, 646, 647; 422/44
See application file for complete search history.

(56) References Cited

U.S. PATENT DOCUMENTS

| | | | |
|---|---|---|---|
| 3,672,509 | A | 6/1972 | Buchmann |
| 3,682,817 | A | 8/1972 | Gunter |
| 4,124,509 | A | 11/1978 | Iijima |
| 5,230,796 | A | 7/1993 | Meulen |
| 2003/0213740 | A1 | 11/2003 | Creasey |
| 2004/0110273 | A1 | 6/2004 | Akers |
| 2004/0195163 | A1 | 10/2004 | Watzele |

FOREIGN PATENT DOCUMENTS

WO 03/049841 6/2003

*Primary Examiner* — John Kim

(74) *Attorney, Agent, or Firm* — Occhiuti Rohlicek & Tsao LLP

(57) ABSTRACT

This invention discloses dialysis devices, related housings, related membranes, related kits, and related methods.

4 Claims, 7 Drawing Sheets

8-in-one dialysis insert

Block of base plate holder

| Sample Name | Plasma chamber (PeakAreaRatio) | Buffer chamber (PeakAreaRatio) | Percentage unbound drug |
|---|---|---|---|
| T0_1um | 0.0504 | | |
| T0.5_1um_replicate1 | 0.0355 | 0.000381 | 1.073239437 |
| T1_1um_replicate1 | 0.0391 | 0.000385 | 0.984654731 |
| T2_1um_replicate1 | 0.0333 | 0.000547 | 1.642642643 |
| T3_1um_replicate1 | 0.0332 | 0.000788 | 2.373493976 |
| T4_1um_replicate1 | 0.0339 | 0.000732 | 2.159292035 |

Protein Binding (Dog plasma) Warfarin_1uM_01

| Sample Name | Plasma chamber (PeakAreaRatio) | Buffer chamber (PeakAreaRatio) | Percentage unbound drug |
|---|---|---|---|
| T0_1um | 0.0504 | | |
| T0.5_1um_replicate2 | 0.0373 | 0.000219 | 0.587131367 |
| T1_1um_replicate2 | 0.0347 | 0.000274 | 0.78962536 |
| T2_1um_replicate2 | 0.035 | 0.000475 | 1.357142857 |
| T3_1um_replicate2 | 0.0334 | 0.000517 | 1.547904192 |
| T4_1um_replicate2 | 0.0316 | 0.000576 | 1.82278481 |

Protein Binding (Dog plasma) Warfarin_1uM_02

DIALYSIS DEVICE

CROSS-REFERENCE TO RELATED APPLICATIONS

This application is a divisional of U.S. patent application Ser. No. 11/281,236, filed Nov. 17, 2005 now U.S. Pat. No. 7,604,739, which claims priority to U.S. Provisional Application Ser. No. 60/629,000, filed on Nov. 18, 2004, the contents of which are incorporated herein by reference.

BACKGROUND

Drugs administered either orally or intravenously bind specific receptors in order to produce expected pharmacologic actions. However, the drugs may also bind to plasma proteins in the circulation. This binding affects the distribution and half-life of the drugs and causes undesirable side effects. The amount of a drug that is free from binding by the proteins is critical for pharmacological action. Ultrafiltration and equilibrium dialysis can be used to determine the concentration of the unbound fraction of the total administered drug.

Conventional equilibrium dialysis requires incubation times as long as 6 to 16 hours to reach a steady state equilibrium. This long incubation time may associate with a volume shift from the dialysate to the plasma-containing solution due to osmotic pressure differences. This shifting can result in plasma protein dilution and has been shown to reduce the in vitro fractional binding of a compound to plasma proteins. Also, the long incubation time may affect the stability of the compound.

Thus, there is a need for an efficient and accurate method and device for the equilibrium dialysis.

SUMMARY

The disclosure provides dialysis devices. They provide improved surface area to volume ratios and consequent accelerated course to equilibrium.

One aspect of the invention features a dialysis device that includes (i) a tubular dialysis membrane defining a chamber, the tubular dialysis membrane having a first terminus and a second terminus, the first terminus defining an opening of the chamber, the opening facing a first direction, the dialysis membrane having an outer surface and an inner surface, the outer surface facing away from the chamber and the inner surface facing the chamber; and (ii) a housing for holding the first and second termini of the dialysis membrane while exposing at least a middle portion of the outer surface of the dialysis membrane, the housing defining a passage having a first opening and a second opening, the first opening of the passage also facing the first direction, the second opening of the passage facing the exposed middle portion of the outer surface of the dialysis membrane, wherein the second opening is connected to a compartment for holding the dialysis membrane. Preferably, one terminus of the dialysis membrane is immobilized at a port such that fluid delivered to the port enters the chamber formed by the membrane. In one embodiment, the port is open. The port can further includes a removable plug. Both termini can be immobilized by two plugs. The chamber formed by the membrane can have a volume of less than 5000, 1000, 500, 300, 200, 50, or 10 µl.

Another aspect of the invention features a housing for holding a dialysis membrane. The membrane defines a chamber and an opening of the chamber; the housing defines a passage or well having a first opening and a second opening. The second opening of the passage faces an outer surface of the dialysis membrane. The passage allows a solution to flow between the first opening and the outer surface of the dialysis membrane through the second opening. The second opening is connected to a compartment for holding the dialysis membrane. The compartment for holding the dialysis membrane can be open or closed. The housing can be made of a fluorocarbon, a polytetrafluoroethylene, a polysulfone, a polyethersulfone, a polyolefin, a polyetheretherketone, a polymethyl methylacrylate, a polystyrene, a polystyrene/acrylonitrile copolymer, a polyvinylidenefluoride, glass, or a mixture thereof.

In one aspect, the invention also features a tubular dialysis membrane for a dialysis device that is held immobile at each end. The membrane can be made of a cellulose, a cellulose acetate, a polytetrafluoroethylene, a polysulfone, a nitrocellulose, a polycarbonate, a polyvinylidenefluoride, a polyolefin, a polyamide, or a mixture thereof. The dialysis membrane can have a molecular weight cut-off of at least 100, 500, 1000, 2000, 5000, 10000, 25000, 50000, 100000, or 300000 Daltons.

In another aspect, the invention further features a dialysis system that includes a plurality of units, e.g., an array of units. Each unit contains a dialysis device described above. Each unit can further have a retainer that contains a fixture adapted to hold the dialysis device. In one example, the dialysis system contains at least 4 rectangular units. The system can include a holder designed to be compatible with 8-well, 12-well, 96-well, 384-well, 1536-well, or other multi-well formats. Dialysis systems can be used for equilibrium and non-equilibrium dialysis.

In yet another aspect, the invention features a housing for a dialysis membrane. The housing includes a first compartment for containing a fluid, a first port for delivering fluid into the first compartment, and a second port for delivering fluid into a chamber that has at least one circumference defined by a dialysis membrane. The circumference can be located in a plane perpendicular to the path of fluid entering a port. The dialysis membrane can be in the first compartment. It can be tubular and immobilized at each end, one of the ends being immobilized at the second port. In one example, the housing contains a third port to which the other terminus is immobilized. The housing can further include a second compartment that is in fluid communication with the first compartment, and the dialysis membrane resides in the second compartment. The housing can also have an upper surface that contains at least one of the ports. The above-mentioned first and second port can be in the same plane, e.g., in the upper surface. The diameter of each port can be less than 50, 40, 30, 20, 10, 5, 3, 2, or 1 mm. The invention features another housing for a dialysis membrane. The housing includes a first compartment for containing a fluid, a first port for delivering fluid into the first compartment; and a second port for delivering fluid into a chamber that comprises a non-planar dialysis membrane.

Within the scope of this invention is a kit containing one or more units of the above-described dialysis devices.

The above-described dialysis devices can be used in a method for to conduct binding assays. The method includes (a) providing plurality of the above-described housing; (b) dispensing in parallel a first buffer into the first ports; and (c) dispensing a sample into a second port. Step (b) is performed before, after, or concurrently with step (c). The first ports and second ports can be in different rows, e.g., in alternating rows. A liquid handling device (e.g., a robot/multi-pipettor) can be used to deliver fluid to one or more ports.

The invention provides a method for conducting binding assays. The method includes adding a first sample to one chamber of at least one well of the above-described dialysis system, where the first sample cannot pass through the membrane; adding a second sample to the lower chamber of the dialysis system, wherein the second sample can pass through the membrane; allowing the first sample and the second sample to equilibrate; and quantitatively or qualitatively assaying the resulting sample.

The details of one or more embodiments of the invention are set forth in the accompanying drawing and the description below. Other features, objects, and advantages of the invention will be apparent from the description and drawing, and from the claims.

DETAILED DESCRIPTION

Dialysis systems can be designed so that they are adaptable to multi-well formats for the simultaneous preparation of multiple samples. For example, they can be adaptable equilibrium dialysis in 8-well, 12-well, 96-well, 384-well, 1536-well, and other multi-well formats.

Figure 1:
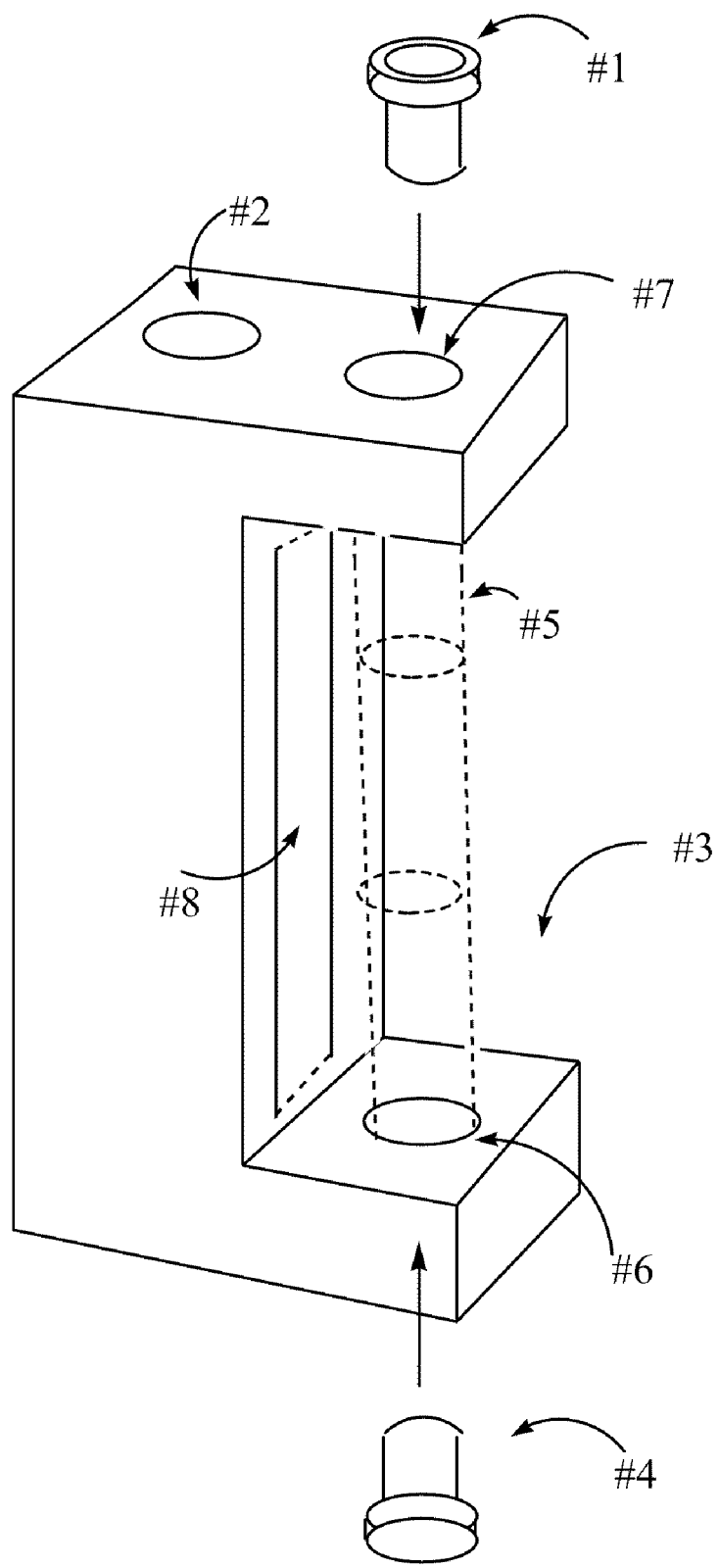
FIG. 1 is a view of an exemplary dialysis device with an open compartment.

Referring to the drawings, FIG. 1 is a view of an exemplary device with an open compartment 3 that houses a cylindrical membrane 5. The cylindrical membrane 5 is held upright using a solid plug 4 at the bottom. The membrane tube slides onto the outside of the solid plug 4, and then the plug is inserted into the bottom base 6. The membrane prolongs through the upper opening 7. A through-hole plug 1 is used to allow the membrane to slide over it and then plug into the upper cavity 7. There is a slot opening 8 connecting the open compartment and the next rounded deep well or passage 2. The opening is sufficiently wide to allow the buffer to flow freely between the rounded deep well 2 and the space outside the cylindrical membrane in the open compartment 3. A sample containing the compound and the plasma proteins is introduced to the inside of the cylindrical membrane from the opening 1. The buffer is introduced through the opening 2, which is connected with the compartment 3. In operation, the dialysis device comprises two fluid-filled chambers, one inside the membrane 5, and the other consisting of the contiguous spaces of the rounded deep well 2 and the open compartment 3.

Figure 2:
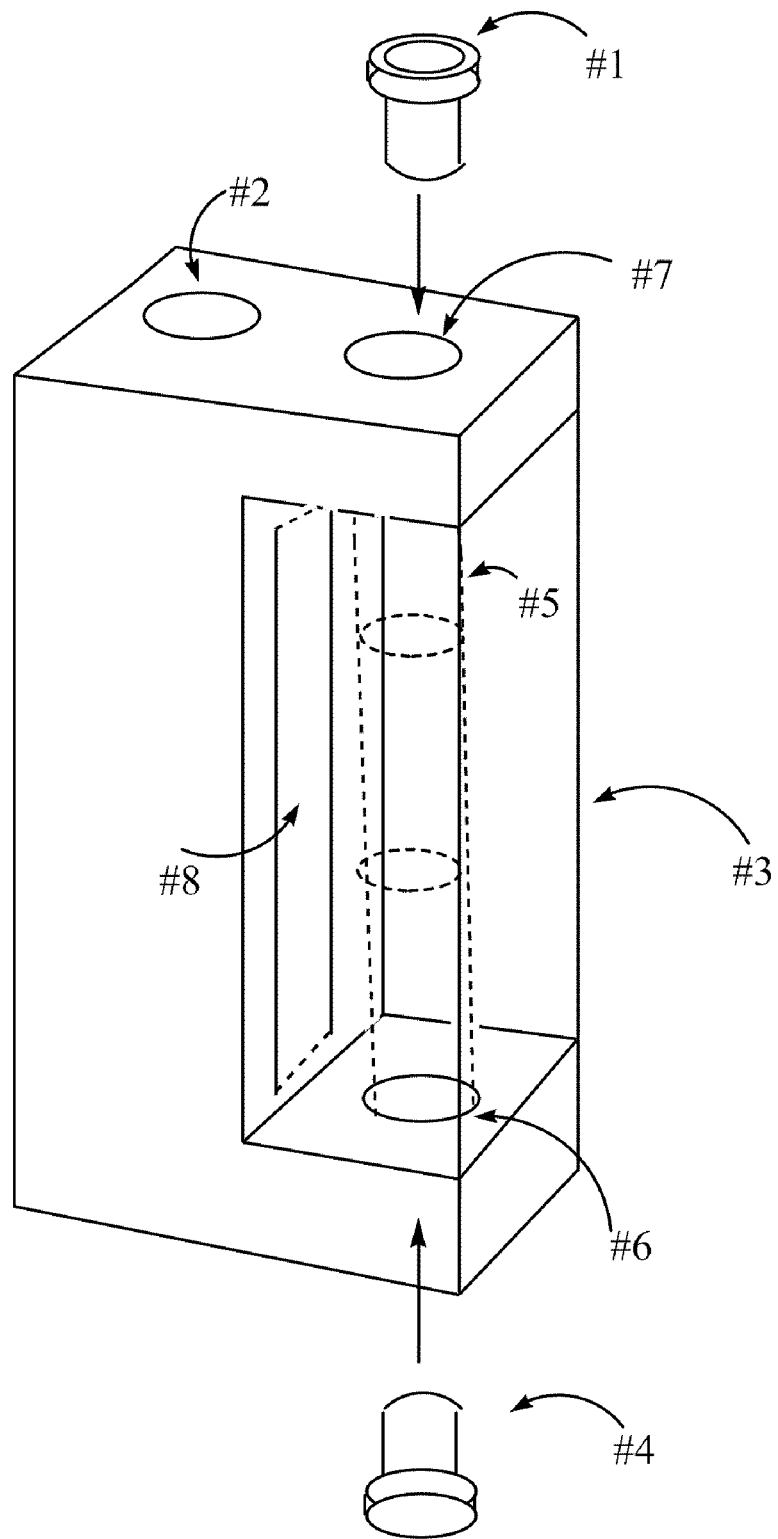
FIG. 2 is a view of an exemplary dialysis device with a closed compartment.

FIG. 2 is a view of an exemplary device with an enclosed compartment 3 that houses a cylindrical membrane 5. The cylindrical membrane 5 is held upright using a solid plug 4 at the bottom. The membrane tube slide onto outside of the solid plug 4, then the plug is inserted into the bottom base 6. The membrane prolongs through the upper opening 7. A through-hole plug 1 is used to allow the membrane to slide over it and then plug into the upper cavity 7. There is a slot opening 8 connecting the compartment 3 and the next rounded deep well 2. The opening is sufficiently wide to allow the buffer to flow freely between the rounded deep well 2 and the space outside the cylindrical membrane in the enclosed compartment 3. A sample containing the compound and the plasma proteins is introduced to the inside of the cylindrical membrane from the opening 1. The buffer is introduced through the opening 2, which is connected with the compartment 3. In operation, the dialysis device comprises two fluid-filled chambers, one inside the membrane 5, and the other consisting of the contiguous spaces of the rounded deep well 2 and the closed compartment 3.

Figure 3:
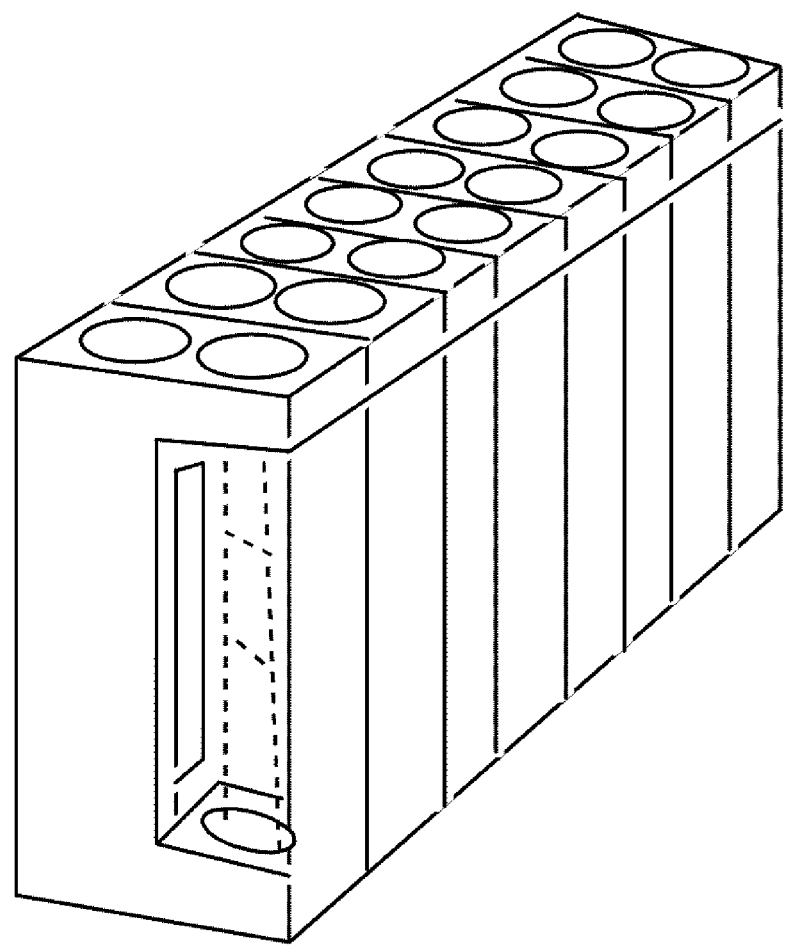
FIG. 3 is a view an exemplary 8-in-1dialysis device insert in a 96-well format.
Figure 4:
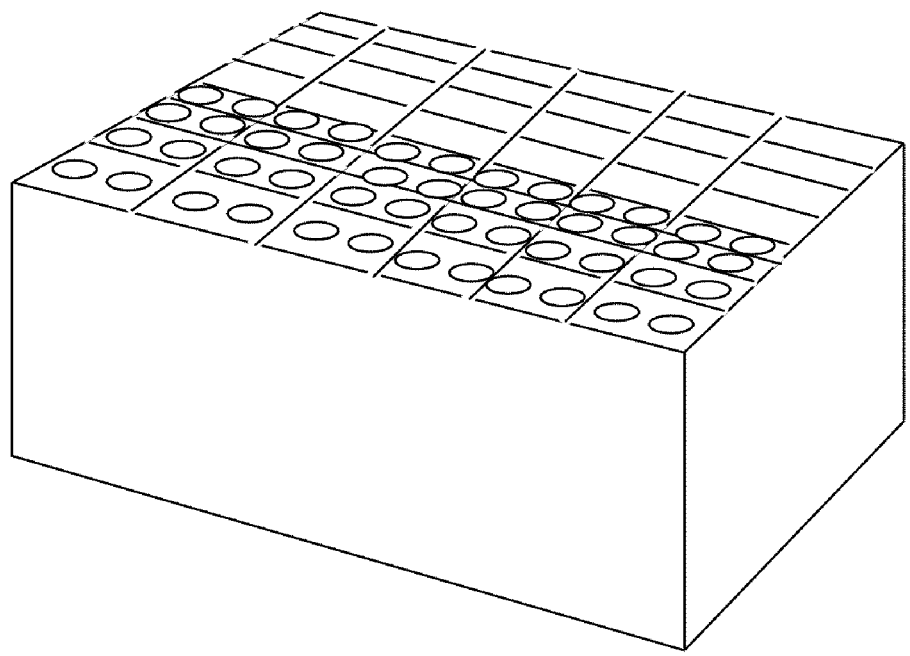
FIG. 4 is a view of an exemplary holder for multiple equilibrium dialysis devices in a 96-well format.

FIG. 4 is a view of a holder for dialysis devices. The size and configuration of the holder can vary. If the holder is to be used with an automated liquid handler, then the dimensions of a conventional deep-well microtiter plate are preferred. A rectangular deep well is designed to hold one unit of the dialysis device, such that the rectangular deep well has a flat bottom which matches the dimensions of the dialysis device. The size of the device can be varied according to the need. Since each unit of the device may occupy two deep square wells of a conventional 96-well plate, the plate is designed to contain 48-deep rectangular wells. Each deep rectangular well is used to hold each unit of the dialysis device. Plates with other common dimensions (e.g., including 8-well, 12-well, 384-well, or 1536-well) can also be used, and the size of the dialysis device can be modified to occupy the holders. However the design of the holder, it can be of dimensions to accommodate the format of an automated liquid handling machine. FIG. 3 is a view an exemplary 8-in-1dialysis device insert in a 96-well format. Six of such inserts can be housed in a base holder as shown in FIG. 5.

Figure 5:
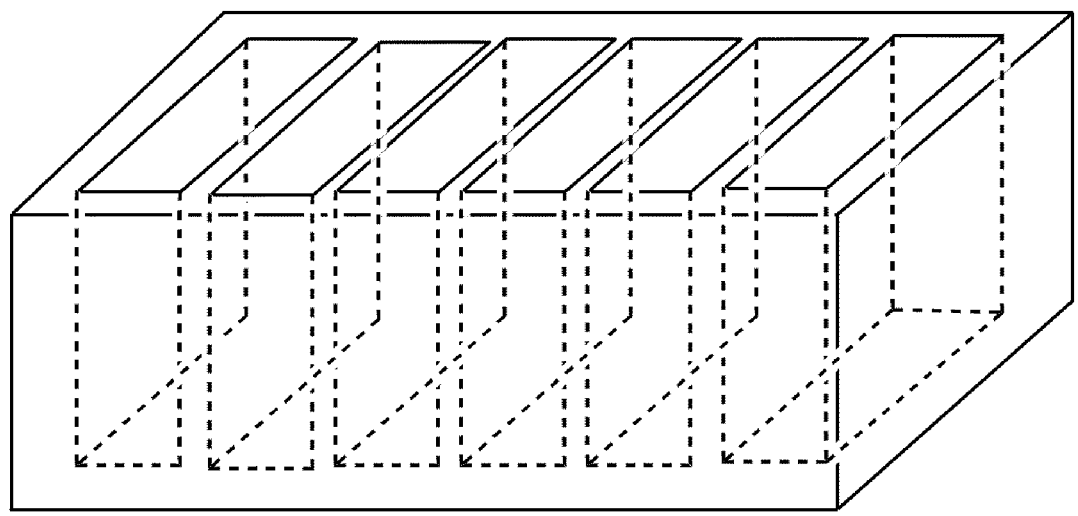
FIG. 5 is a view an exemplary block of base plate holder for six 8-in-1dialysis devices in a 96-well format.

A multi-well equilibrium dialysis system can comprise multiple units of a dialysis device of FIG. 1, 2, or 3, e.g., in a holder of FIG. 4 or 5. A multi-well equilibrium dialysis system allows for the simultaneous preparation of multiple samples with applications including, but not limited to, high throughput screening, binding assays, and bio-molecule interactions (e.g., protein-protein interactions).

Dialysis systems can be compatible with 8-well, 12-well, 96-well, 384-well, 1536-well, and other multi-well formats. For example, a dialysis system compatible with an 8-well format will contain 4 rectangular wells; a dialysis system compatible with a 12-well format will contain 6 rectangular wells; a dialysis system compatible with a 96-well format will contain 48 rectangular wells; a dialysis system compatible with a 384-well format will contain 192 rectangular wells; a dialysis system compatible with a 1536-well format will contain 768 rectangular wells. The long axes of the dialysis devices can be arranged along either the long or short axis of the holder.

The housing of the device may be made of any material known in the art. Exemplary materials include fluorocarbons, polytetrafluoroethylenes (e.g., TEFLON® by DuPont), polyolefins (e.g., polypropylene, polyethylene, and mixtures thereof), polysulfones, polyethersulfones, polyetheretherketones, polymethyl methacrylates, polystyrenes, polystyrene/actylonitrile copolymers, polyvinylidenefluorides (PVDF), glasses, and the like.

The semi-permeable membrane 5 may be of any molecular weight cut-off known in the art, and may be of any material known in the art. Exemplary molecular weight cut-offs are, for example, from 100 Daltons to 10 million Daltons. Membranes may have molecular weight cut-offs of, for example, 100 Daltons, 500 Daltons, 1,000 Daltons, 2,000 Daltons, 5,000 Daltons, 10,000 Daltons, 25,000 Daltons, 50,000 Daltons, 100,000 Daltons, and 300,000 Daltons. Alternatively, the membrane may have a pore size from about 0.01 microns to about 1 micron. Membranes may have pore sizes of, for example, 0.01 microns, 0.05 microns or 0.60 microns.

Exemplary membrane materials include celluloses (e.g., regenerated celluloses), cellulose acetates, polytetrafuloroethylenes (e.g., TEFLON® by DuPont), polysulfones, nitrocelluloses, polycarbonates, polyolefins (e.g., polypropylene, polyethylene, and mixtures thereof), polyamides, polyvinylidenefluorides, and the like.

The term "cylindrical" as used herein to describe the equilibrium dialysis membrane is defined as any tubular configuration, for example, a cube, cylinder, rectangular prism, pentagonal prism, triangular prism, hexagonal prism, cone, and the like.

The plugs that hold the cylindrical membrane may be made of any material known in the art. Exemplary materials include cork, plastic, rubber, silicone, and the like.

The shape of the upper plug 1 and corresponding cavity 7, as well the shape of the lower plug 4 and corresponding cavity 6, may independently be, for example, a cube, cylinder, rectangular prism, pentagonal prism, triangular prism, hexagonal prism, cone, and the like.

The volume of the chamber consisting of the membrane-enclosed space 5 and the chamber comprising the rounded deep well 2 contiguous with the compartment 3 may independently be, for example, from about 10 Tl to about 5,000 Tl. The volumes of the two chambers may range from about 10 Tl to about 200 Tl; or from about 50 Tl to about 200 Tl; or from about 25 Tl to about 300 Tl; or from about 500 Tl to about 1,500 Tl; or from about 3,000 Tl to about 5,000 Tl. In the preferred embodiment, the volume of the chamber consisting of the membrane enclosed space 5 and the chamber comprising the rounded deep well 2 contiguous with the compartment 3 may independently be from about 500 Tl to about 1500 Tl.

Each unit of the multi-well dialysis system may have membranes that have different molecular weight cut-offs and/or that are made of different materials.

Kits can be assembled that include one or more dialysis systems described herein. The kit can be a package comprising one or more dialysis devices and holders along with manuals describing their use.

One method of using a dialysis system described herein to conduct a binding assay (e.g., receptor-ligand assay) includes the following: one sample chamber may be filled with a protein sample (e.g., receptor). The protein sample contains molecules that are too large to pass through the pores of the membrane. The second chamber is filled with small molecules (e.g., ligand) that can pass through the pores of the membrane. When this system is allowed to equilibrate, the small molecules will be present in both chambers, i.e., both inside and outside the membrane-enclosed space. If the small molecules bind to the protein, the state of equilibrium will be affected such that more small molecules will be present in the protein sample chamber than in the small molecule sample chamber. During and upon completion of equilibrium dialysis, quantitative and/or qualitative assays can be performed to further study the samples. This method is frequently used in new drug discovery methods. By choosing appropriately-sized membranes, equilibrium dialysis may also be used to study DNA-protein interactions, protein-protein interactions, and many other interactions between bio-molecules and other molecules. (Either the compartment defined by the membrane or the surrounding compartment can contain the sample).

The dialysis system described herein can be used with conventional liquid handling systems. These systems typically operate using a standard plate configuration, e.g., a 96-well plate with dimensions of 8 wells by 12 wells. The dialysis system also can be arranged to take advantage of this configuration. The individual units can all be placed into the holder with the same orientation, such that there are alternating rows of ports 1 and ports 2.

In, for example, a 96 well-type configuration, the units can be arranged 8 rows by 6 columns or 12 rows by 4 columns. Using this type of configuration, the array of port openings in the dialysis system corresponds to the positions of the wells of a standard 96-well plate. The ports can be aligned. For example, alternating rows can include ports for buffer and ports for sample, respectively. In another example, the ports alternate in the columns.

A similar configuration can be produced such that the array of port openings in the dialysis system corresponds to the positions of the wells of any other standard plate configuration (e.g., 8-well, 12-well, 384-well, 1536-well). This can allow a conventional liquid handling system to be easily programmed to fill, sample, and perform other manipulations on the dialysis system.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE

Figure 6:
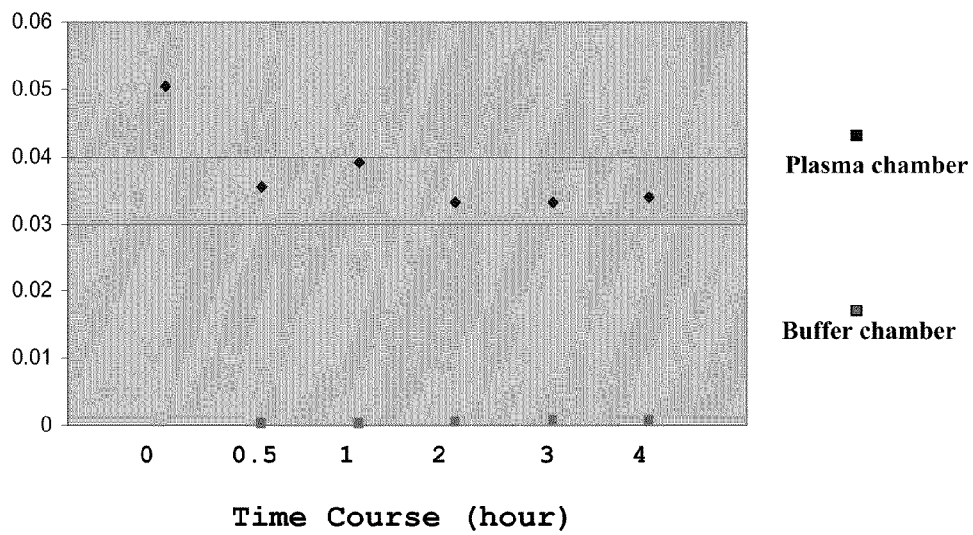
FIG. 6 is data from one replicate of an equilibrium dialysis procedure. The upper panel is a table depicting relative concentrations of warfarin in the chambers over time. The lower panel is a graph depicting relative concentrations of warfarin in the chambers over time.
Figure 7:
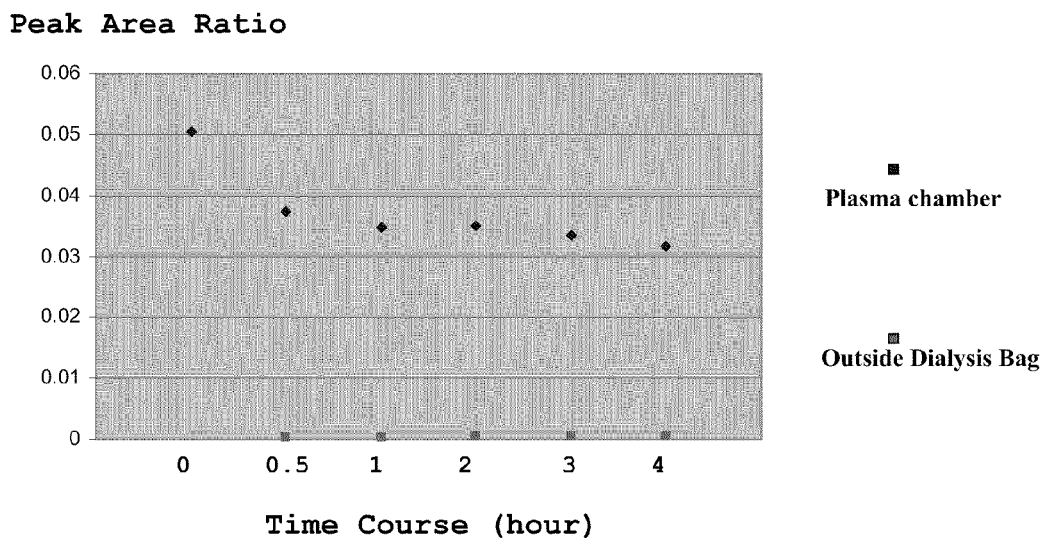
FIG. 7 is data from one replicate of an exemplary equilibrium dialysis procedure. The upper panel is a table depicting relative concentrations of warfarin in the chambers over time. The lower panel is a graph depicting relative concentrations of warfarin in the chambers over time.

One dialysis device was used in an equilibrium dialysis study to measure plasma protein binding of warfarin. A 0.1 M warfarin solution was prepared by dissolving 0.154 g of warfarin in 5 ml of phosphate buffered salts (PBS). The pH was adjusted with 400 Tl of 6 M NaOH to a final volume of 5.761 ml and a final concentration of 86.8 mM. The warfarin solution was then diluted to 1 mM before adding to the plasma solution. 2.2 Tl of 1 mM warfarin was added to 2.2 ml plasma to make 1 TM final concentration of warfarin in the plasma. 1 ml of the warfarin-containing dog plasma was added inside the cylindrical membrane of each dialysis device and 1 ml of PBS to outside of the membrane. The filled device was placed in a 37° C. incubator with gentle shaking 100 Tl samples were withdrawn separately from the plasma and the buffer chambers at 0.5, 1, 2, 3, and 4 h intervals. To the plasma sample was added 100 μl of blank buffer. To the buffer sample was added 100 μl of blank plasma. After mixing, 50 μl of the plasma sample was withdrawn. To the plasma sample (50 μl) was added 450 μl of 1:1 ratio of plasma/buffer solution to make a 10-fold dilution. The sample from the buffer was not diluted. 200 μl acetonitrile was added to 200 μl each of the samples from plasma and the buffer. The mixtures were vortexed and then centrifuged at 13,000 rpm for 3 min. The resulting extracts were analyzed using an API-40003 LC/MS/MS system (Applied Biosciences/MDS SCIEX). The results show consistency of equilibrium curve almost within 1 hour. The experiment was conducted in duplicate. The ratio of protein binding was close to 99% as shown in the charts indicated in FIGS. 6 and 7. The results show that the dialysis reached equilibrium state within 30 minutes.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An apparatus for holding a tubular dialysis membrane, the apparatus comprising a first compartment and a second compartment, wherein the first compartment is configured to immobilize the tubular dialysis membrane and includes plug means for retaining liquid in the tubular dialysis membrane, and the second compartment includes an inlet and a slot opening, the slot opening configured to face the tubular dialysis membrane in the first compartment, permitting a solution entering the inlet to flow therethrough to reach the tubular dialysis membrane in the first compartment.

2. The apparatus of claim 1, wherein the apparatus is configured to fit tightly within a closed chamber.

3. The apparatus of claim 2, wherein the apparatus is made of a fluorocarbon, a polytetrafluoroethylene, a polysulfone, a polyethersulfone, a polyolefin, a polyetheretherketone, a polymethyl methylacrylate, a polystyrene, a polystyrene/acrylonitrile copolymer, a polyvinylidenefluoride, glass, or a mixture thereof.

4. The apparatus of claim 1, wherein the apparatus is made of a fluorocarbon, a polytetrafluoroethylene, a polysulfone, a polyethersulfone, a polyolefin, a polyetheretherketone, a polymethyl methylacrylate, a polystyrene, a polystyrene/acrylonitrile copolymer, a polyvinylidenefluoride, glass, or a mixture thereof.

* * * * *